(12) United States Patent
Wangler (10) Patent No.: US 10,232,094 B2
(45) Date of Patent: Mar. 19, 2019

(54) CASSETTE MODULE

(71) Applicant: Oertli-Instrumente AG, Berneck (CH)

(72) Inventor: Christoph Wangler, Rorschacherberg (CH)

(73) Assignee: OERTLI-INSTRUMENTE AG, Berneck (CH)

( * ) Notice: Subject to any disclaimer, the term of this patent is extended or adjusted under 35 U.S.C. 154(b) by 684 days.

(21) Appl. No.: 14/656,145

(22) Filed: Mar. 12, 2015

(65) Prior Publication Data

US 2015/0258255 A1 Sep. 17, 2015

(30) Foreign Application Priority Data

Mar. 13, 2014 (EP) ..................................... 14159377

(51) Int. Cl.
*A61M 1/00* (2006.01)
*A61F 9/007* (2006.01)

(52) U.S. Cl.
CPC ....... *A61M 1/0003* (2013.01); *A61F 9/00736* (2013.01); *A61M 1/0005* (2013.01); *A61M 1/0023* (2013.01); *A61M 2205/0216* (2013.01); *A61M 2205/12* (2013.01); *A61M 2205/121* (2013.01); *A61M 2210/0612* (2013.01)

(58) Field of Classification Search
CPC .... A61M 1/00; A61M 1/0001; A61M 1/0003; A61M 1/0005; A61M 1/0023; A61M 2205/12; A61F 9/00736
See application file for complete search history.

(56) References Cited

U.S. PATENT DOCUMENTS

| | | | | |
|---|---|---|---|---|
| 4,735,610 A | * | 4/1988 | Akkas | A61M 1/0062 604/119 |
| 4,855,064 A | * | 8/1989 | Schlein | A61M 1/00 210/205 |
| 5,499,969 A | * | 3/1996 | Beuchat | A61M 1/0058 128/DIG. 12 |
| 7,833,206 B1 | | 11/2010 | Lumpkin et al. | |
| 2008/0114301 A1 | * | 5/2008 | Bandhauer | A61M 1/0049 604/153 |

(Continued)

FOREIGN PATENT DOCUMENTS

| | | |
|---|---|---|
| WO | 2008060958 A1 | 5/2008 |
| WO | 2010054145 A1 | 5/2010 |
| WO | 2010056972 A1 | 5/2010 |

*Primary Examiner* — Ariana Zimbouski
(74) *Attorney, Agent, or Firm* — The Webb Law Firm (57) ABSTRACT

A cassette module (1), in particular an ophthalmological cassette module (1), serves for receiving material and/or liquids aspirated during an operation and for insertion into a container chamber (8) of a suction module (19). The cassette module (1) comprises a container (4) with a container wall (3) that delimits a receiving space (33) for receiving the liquids, wherein the container (4) can be inserted into the container chamber (8), wherein the container (4) has at least one inlet opening (36) extending through the container wall (3), through which inlet opening (36) the material and/or the liquid can be delivered to the receiving space (33) of the container (4), and wherein the container (4) has at least one vacuum opening (25) which extends through the container wall (3) and by way of which the receiving space (33) can be subjected to an underpressure built up in the container chamber (8).

21 Claims, 5 Drawing Sheets (56) References Cited

U.S. PATENT DOCUMENTS

2009/0012493 A1* 1/2009 Harig ................. A61M 1/0003
604/404
2012/0277552 A1* 11/2012 Gerber ................ A61B 5/0031
600/309

* cited by examiner

CASSETTE MODULE

CROSS REFERENCE TO RELATED APPLICATION

This application claims priority to European Patent Application No. 14 159 377.2 filed Mar. 13, 2014, the disclosure of which is hereby incorporated in its entirety by reference.

BACKGROUND OF THE INVENTION

Field of the Invention

The present invention relates to a cassette module, in particular an ophthalmological cassette module, for receiving aspirated material, in particular liquids. The invention further relates to a suction system with the cassette module.

Description of Related Art

In surgical appliances for eye surgery, various types of discharge containers for collecting material aspirated from the eye are known in the prior art. These are of different designs depending on the vacuum pump technology that is used.

In appliances with vacuum pumps operating according to the Venturi principle, a vacuum of up to 700 mmHg is usually present in the discharge container, as a result of which the latter serves not only for receiving the aspirated materials but also as vacuum container. In this case, the discharge container has to be dimensionally stable in design and have thick walls, in order to ensure that the container can be used as vacuum container at these pressure differences. As a result of this design, a comparatively large amount of material is needed to produce the discharge containers, and this has a negative impact on costs, both in terms of procurement and of disposal. Moreover, disposable discharge containers, which are increasingly being used on account of the enhanced patient safety against infections and the easier procedures in the operating room, require a relatively large amount of material.

Moreover, the production costs as such are also relatively high, since the discharge containers are usually produced from several parts that are connected to one another by ultrasonic welding. This further increases the costs.

Moreover, in some of the known surgical appliances, all the sensors and actuators, which require mechanical contact with elements of the cassette, e.g. pressure sensors and flow sensors, engage directly on the vacuum container. For good and reproducible measurement accuracy, and therefore precise electronic regulation of the fluidics, these sensors require stable mechanical interfaces. In this case, therefore, the vacuum container has to be made very stiff, in order to avoid deformations caused by the vacuum build-up, which deformations would otherwise adversely affect the functionality of the mechatronic and fluidic system.

SUMMARY OF THE INVENTION

It is an object of the invention to make available a cassette module or discharge container, particularly for use in eye surgery for receiving material or liquids aspirated from the eye during an operation on the eye, which cassette module overcomes the disadvantages of the prior art. In particular, however, the cassette module should be able to be produced as efficiently as possible and to be disposed of in as environmentally friendly a way as possible.

Accordingly, a cassette module, in particular an ophthalmological cassette module, serves for receiving aspirated liquids or material. The cassette module is inserted into a container chamber of a suction module and is there subjected to a vacuum. The cassette module comprises a container with a container wall that delimits a receiving space for receiving the liquids, wherein the container can be inserted into the container chamber. The container has at least one inlet opening extending through the container wall, through which inlet opening the liquid can be delivered to the receiving space of the container. Moreover, the container has at least one vacuum opening which extends through the container wall and by way of which the receiving space can be subjected to an underpressure.

By virtue of the fact that a vacuum can be applied to the container via the at least one vacuum opening, it is possible to create a container that is of a very simple design. In this way, the cassette module can be produced inexpensively and efficiently.

The at least one vacuum opening is preferably designed in such a way that it constitutes a simple break through the container wall. A simple break-through is understood as an opening that extends all the way from one surface of the container wall to the other surface of the container wall, without any flange-like or similar elements extending away from either surface. The surfaces of the side wall typically lie substantially parallel to each other. For production-related reasons, the surfaces may be arranged at a shallow angle to each other, in the range of ca. 1° to at most 2°. This too can be designated as a parallel configuration.

When the container is situated in the container chamber, the at least one vacuum opening preferably lies at a distance from the walls of the container chamber. A vacuum in the container chamber also acts in the receiving space of the container via the vacuum opening.

Particularly preferably, the cassette module moreover has a sealing surface which extends around the outside of the container wall and by which a sealing action can be provided between the container chamber and the container protruding into the container chamber. On account of the sealing action, the receiving space and the container chamber are closed off from the environment when the cassette module is inserted. In this way, the container chamber can be subjected to an underpressure, said underpressure also being correspondingly present in the receiving space via the vacuum opening.

Preferably, the sealing surface runs in a plane which preferably extends in an edge area through the container or which preferably extends through a side wall of the container.

Preferably, a seal extending around the container is arranged on the sealing surface. This has the advantage that no seal has to be present on the suction system, and the seal on the cassette module is a disposable element, as a result of which there is no need for any maintenance of the seal.

Alternatively, the sealing surface can be brought into contact with a seal arranged on the suction module. In this alternative, the seal is therefore part of the suction module.

Preferably, the cassette module comprises at least one port for connection to an operating system, which port leads into the inlet opening and connects a fluid line to the port. By way of the fluid line, the fluid passes through the inlet opening into the receiving space of the container.

Preferably, the cassette module moreover comprises a function module, which is connected to the container. The function module serves to receive diverse elements for various functions.

Seen from the direction of the sealing surface, the container preferably extends in a first direction and the function module preferably extends in a second direction that is different from or counter to the first direction. The sealing surface thus forms a kind of separating surface between function module and cassette module.

Preferably, the container wall of the container is made of plastic and has a wall thickness of 0.5 to 1.5 mm, particularly preferably of 0.7 to 1.2 mm. Wall thicknesses in this range are considered unstable when a vacuum acts on the inside of the container. Under equal pressure conditions on the inside and outside, the container has a comparatively stable form, such that it is easy to handle. In the inserted state, the same underpressure prevails outside the container and in the receiving space.

Preferably, the container delimiting the receiving space is provided by a circumferential side wall, a rear wall connected to the side wall, and a lid arranged opposite the rear wall, in which case the side wall and the rear wall are preferably formed in one piece, and the cover is preferably cohesively bonded to the side wall. Side wall, rear wall and lid thus provide the container wall, which surrounds the receiving space substantially completely. Apart from the vacuum opening and the inlet opening, the container is designed to be leaktight to fluid.

In a particularly preferred embodiment, when the container is inserted into a container chamber of a suction module, the container wall lies at a distance from the walls of the container chamber. This applies particularly in the area of the vacuum opening.

In another embodiment, the container wall is in contact with the walls of the container chamber. In the area of the vacuum opening, however, the container wall is preferably at a slight distance from the walls of the container chamber.

Preferably, the container is made of plastic and has an inherent stability. Alternatively, the container made of plastic can also have the form of a film. The design as a film moreover reduces the weight. The thickness of the film is smaller than the abovementioned wall thickness or lies in the lower range of the abovementioned wall thicknesses.

As regards the number of the vacuum openings, the container has at least one vacuum opening or several. The vacuum opening allows the vacuum to be applied in the interior of the container. In the inserted state, the vacuum opening lies preferably in the area where the vacuum port enters the container chamber.

Preferably, the function module is formed integrally on the container, and the function module is preferably closed by the lid.

Function module and container form substantially a one-piece and integral unit composed of container and function module.

Preferably, the fluid line comprises a hose section that is guided over a concave rounding on the function module, in which case a peristaltic pump protrudes with the pump wheel into the concave rounding. The flow of fluid in the fluid line can be assisted or provided by the peristaltic pump. This hose section is connected to said port and leads through the inlet opening into the container.

Preferably, the fluid line is guided on the function module partly by webs protruding from a plate and by a side wall lying on the webs and secured to the plate. In other embodiments, it is also possible to dispense with the plate.

Preferably, the cassette module has an emergency drainage opening. By way of the emergency drainage opening, the liquid can be drained from the container when the latter is full.

A suction system, in particular an ophthalmological suction system, for receiving material, such as liquids, aspirated during an operation comprises a suction module and a cassette module according to the above description. The suction module comprises a container chamber which is delimited by chamber walls and which is used for receiving the container of the cassette module, which container chamber is accessible via an insert opening, and a pump for generating an underpressure in the container chamber. The underpressure acts on the container via the vacuum opening.

The insert opening of the container chamber is closed in an airtight manner by parts of the cassette module, in particular by the function module and/or the lid. Thus, the cassette module serves not only for receiving the aspirated liquid but also for closing the container chamber in an airtight manner.

Preferably, the container chamber has a shape identical to the outer shape of the container, such that the container wall of the container bears on the chamber wall. Alternatively, the container chamber has a shape similar to the outer shape of the container, in which case the container wall of the container lies at a distance from the chamber wall.

Preferably, the container wall lies at a distance from the chamber wall in the area of the vacuum openings, such that the receiving space can be readily exposed to the vacuum provided in the container chamber.

Preferably, the suction module comprises a plane wall, which provides a sealing surface extending around the container chamber for contact with a seal arranged in the area of the sealing surface of the cassette module. Alternatively, the suction module comprises a plane wall on which a seal for contact with the base plate is arranged extending around the container chamber.

The seal can also be arranged in a groove that extends into the sealing surface of the suction module or of the cassette module.

Preferably, the suction module moreover comprises an underpressure port arranged in the chamber wall, wherein the underpressure port lies in the area of the at least one vacuum opening when the cassette module is inserted, such that the underpressure port can cooperate with the vacuum opening. The underpressure port is connected fluidically, in particular pneumatically, to a pump.

Preferably, the cassette module can be pushed into the suction module in a rectilinearly oriented insertion movement.

BRIEF DESCRIPTION OF THE DRAWINGS

Preferred embodiments of the invention are described below with reference to the drawings, which serve only for illustration and are not to be interpreted as limiting the invention. In the drawings.

DESCRIPTION OF PREFERRED EMBODIMENTS

Figure 1:
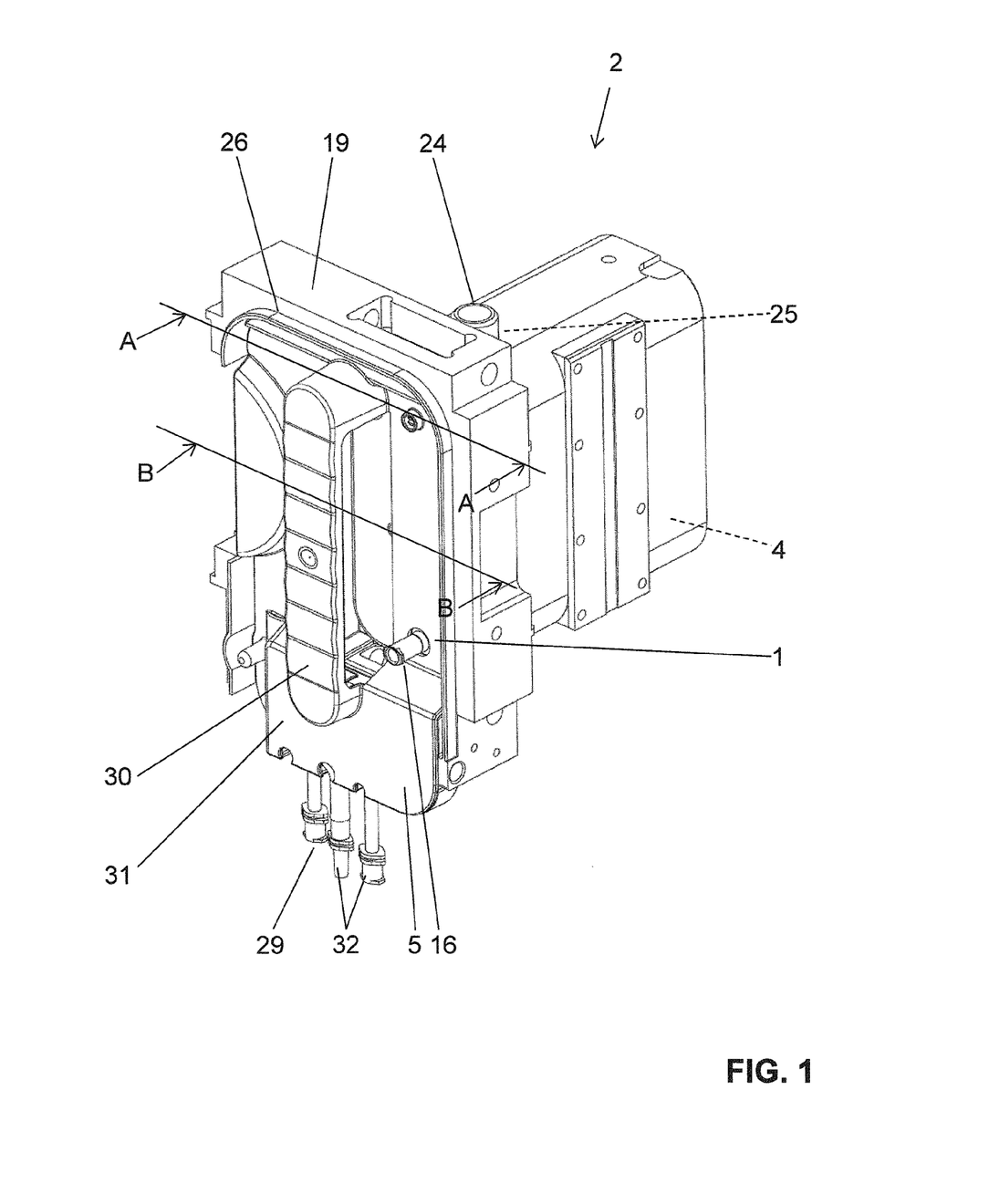
FIG. 1 shows a perspective view of an embodiment of a suction system with a suction module and with a cassette module.

FIG. 1 shows a suction system 2 with a suction module 19, and with a cassette module 1 inserted into the suction module 19. The suction system 2 is preferably an ophthalmological suction system. The suction system serves for receiving liquids and/or materials that are aspirated during operations, in particular during eye operations. Before an operation, the cassette module 1 is inserted into the suction module 19. During the operation, parts of the cassette module 1 are subjected to underpressure and serve for receiving the material or the liquids, and, after the operation, the cassette module 1 is removed again. As is shown in the following description, the cassette module 1 is advantageously provided as a disposable module, as a result of which it is unnecessary to clean the cassette module 1. The cassette module 1 is thus preferably used for just a single operation.

Figures 2, 3:
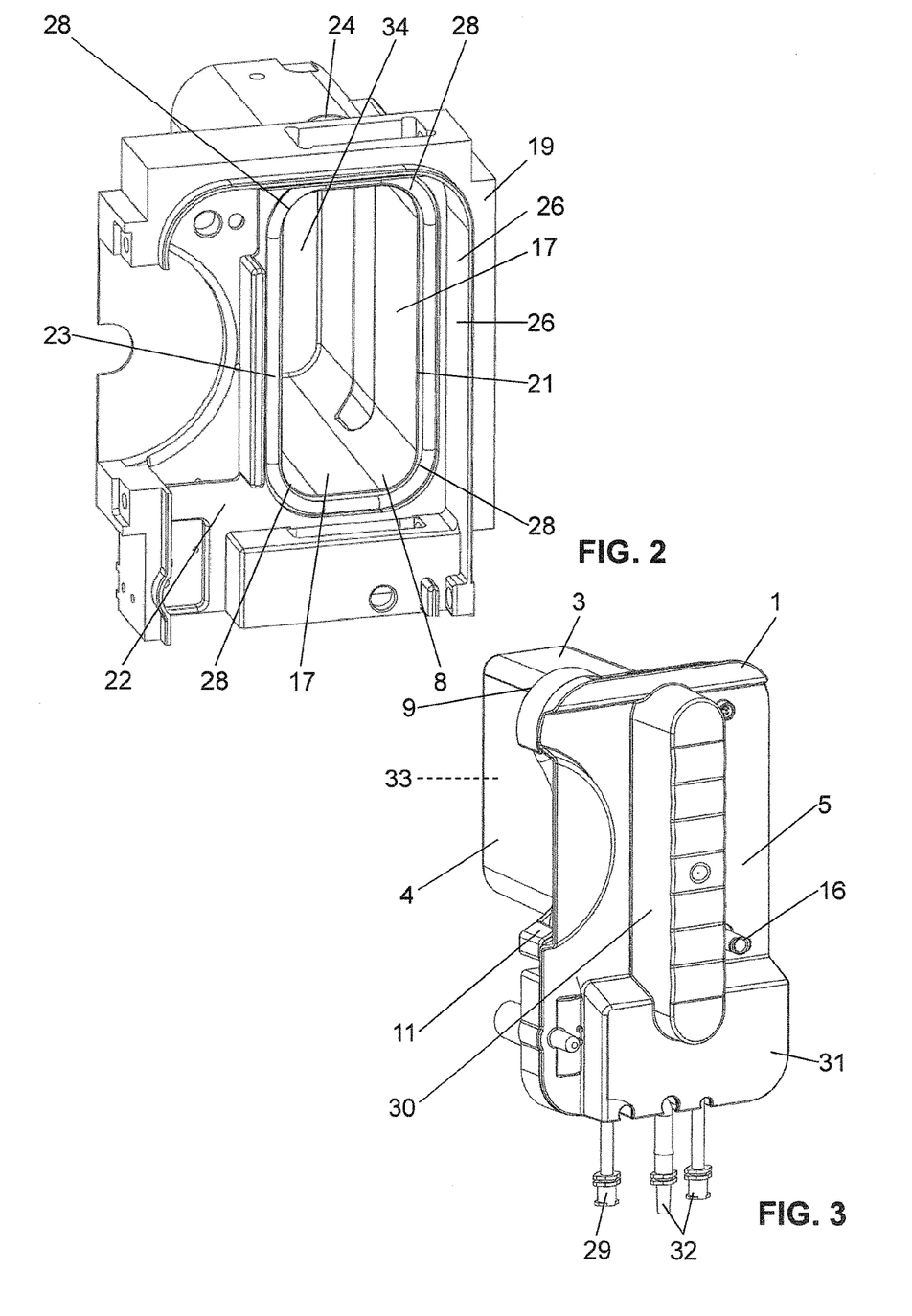
FIG. 2 shows a perspective view of the suction module according to FIG. 1 without the cassette module.
FIG. 3 shows a perspective view of the cassette module of FIG. 1.

In FIG. 2, the suction module 19 is shown without the cassette module 1. The suction module 19 basically comprises a container chamber 8 which is delimited by side walls 17 and which serves to receive the cassette module 1, in particular to receive the container 4. The container chamber 8 is accessible via an insert opening 21. The side walls 17 here have rounded corners 28. The container chamber 8 has substantially a cuboid shape. Opposite the insert opening 21, the container chamber 8 has a rear wall 34. As regards the rear wall 34, it may also be said that the side walls 17 extend substantially perpendicularly from the rear wall 34.

It can likewise be seen from FIG. 2 that the suction module 19 comprises, in addition to the container chamber 8, a further optional chamber 26 for receiving a function module 5, which can likewise be part of the cassette module 1. The optional chamber 26 lies in front of the container chamber 8, as seen in the direction of insertion, and here extends laterally beyond the container chamber 8.

In FIG. 3, the cassette module 1 is shown, wherein the cassette module 1 can be inserted into the suction module 19 according to FIGS. 1 and 2. The cassette module 1 comprises a container 4, which is delimited by a container wall 3. The container wall 3 delimits a receiving space 33, which serves for receiving the aspirated material or the liquid. In the embodiment shown, the receiving space 33 is delimited by a circumferential side wall 38, a rear wall 39 connected to the side wall 38, and a lid 37 arranged opposite the rear wall 39. Side wall 38 and rear wall 39 are preferably formed in one piece, and the lid 37 is preferably cohesively connected to the side wall 38. The side wall 38, the rear wall 39 and the lid 37 provide the container wall 3.

Figures 4, 5:
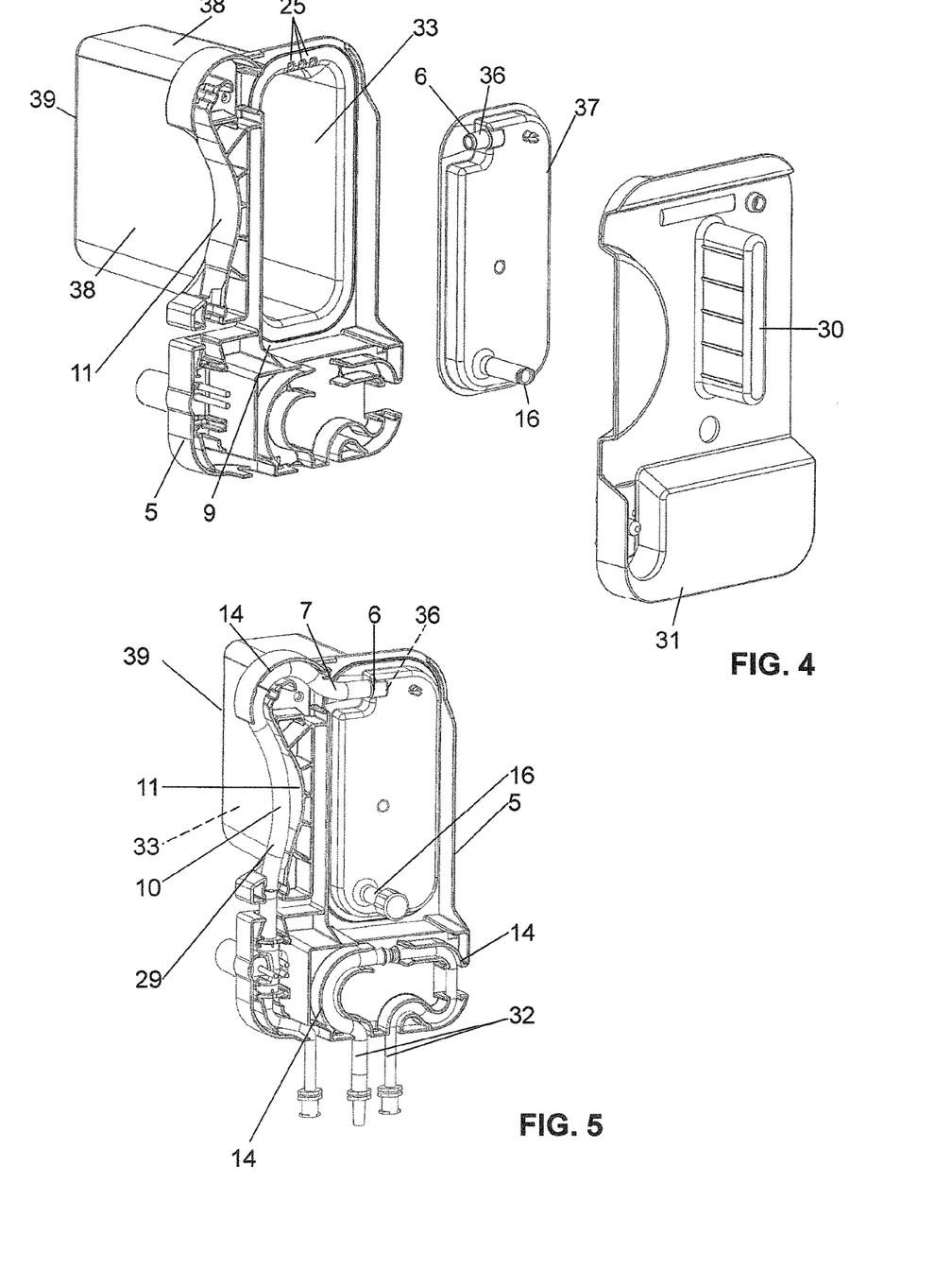
FIG. 4 shows an exploded view of the cassette module of FIG. 1, with another variant of the lid being shown.
FIG. 5 shows another perspective view of the cassette module of FIG. 1.

FIG. 4 shows an exploded view of the cassette module 1. The container 4 has at least one inlet opening 36 extending through the container wall 3, through which inlet opening 36 the liquid can be delivered to the receiving space 33 of the container 4. Here, the inlet opening 36 is arranged in the lid 37. In other embodiments, the inlet opening 36 can lie at any desired position in the container wall 3. Moreover, the container 4 has at least one vacuum opening 25, which extends through the container wall 3 and by way of which the receiving space 33 can be subjected to an underpressure.

The cassette module 1 has at least one port 6 for connection to an operating system, and at least one fluid line 7 adjoining the port 6 and leading into the container. The port 6 has the inlet opening 36. The fluid line 7 passes through an inlet opening 36 into the receiving space 33. The fluid line 7 can be seen particularly clearly in FIG. 5. The fluid line 7 is preferably a hose 29.

Moreover, the cassette module 1 comprises a function module 5, which is connected to the container 4. The function module 5 can be seen clearly in FIGS. 3 to 5. Moreover, additional hoses 32 are accommodated in the function module 5. The hoses 32 have a wide variety of functions but basically serve to support the suction process. The additional hoses 32 serve as feed elements, for example for infusion liquids.

The container 4 and the container wall 3 can be provided with a comparatively thin wall thickness. Since the container wall 3, in the inserted state, is subjected to an underpressure from outside and from inside, no forces act on the container in suction mode. To this extent, the container 4 can also be designed in such a way that it is not vacuum-tight.

In one variant, the container 4 is preferably designed in such a way that it comes into contact with the side walls 17 of the suction module 19, in which case the container walls 3 are supported on the side walls 17. In another variant, this support is not needed, and the container 4 can lie at a distance from the walls 17. This variant is advantageous since the application of the vacuum is easier to manage.

The container wall 3 is preferably made of a plastic and has a wall thickness of 0.5 to 1.5 mm, particularly preferably of 0.7 to 1.2 mm. Such walls are typically to be regarded as unstable when an underpressure acts in the receiving space 33. In an alternative embodiment, the container 4 can also be made of plastic in the form of a film.

Figure 6:
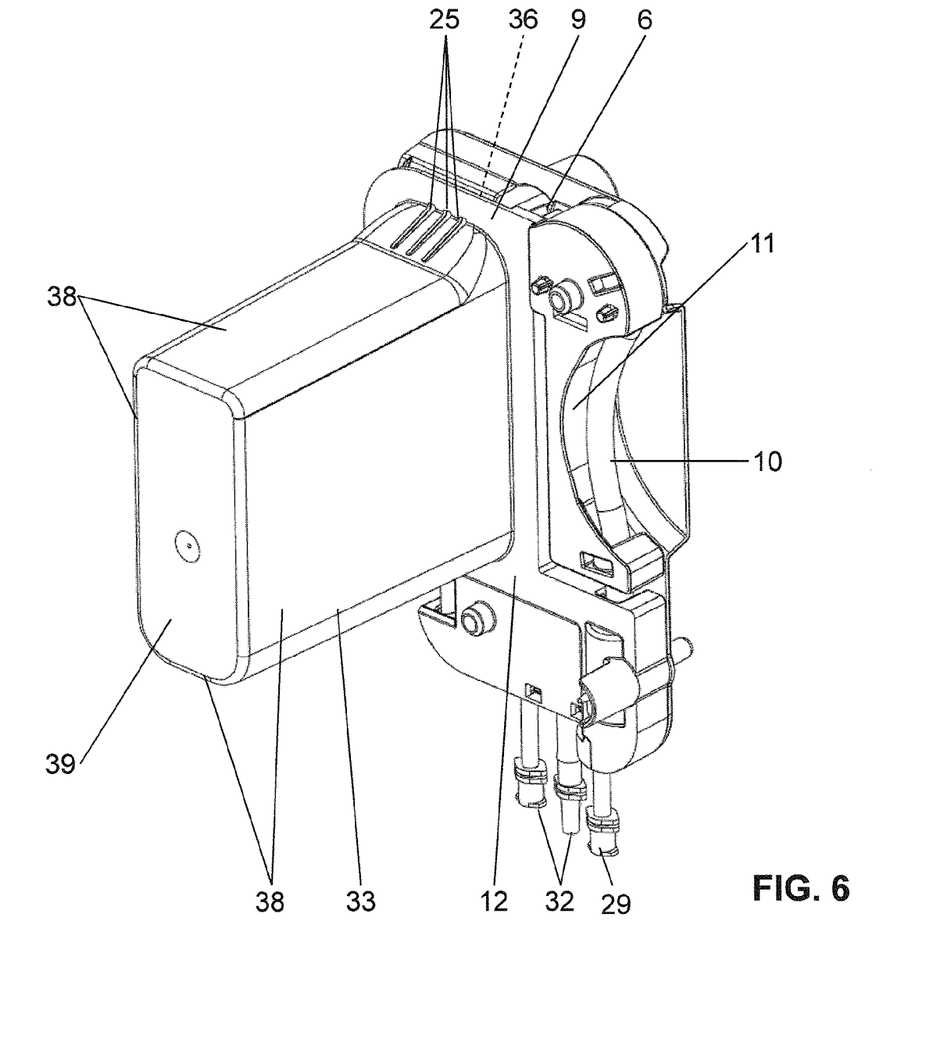
FIG. 6 shows a rear view of the cassette module of FIG. 1.

The at least one vacuum opening 25 can be clearly seen from FIG. 6. In this embodiment, several slits are arranged parallel to one another as vacuum openings 25. In other embodiments, it is also possible for several vacuum openings 25 to be arranged in a grid. They can also be referred to as a set of vacuum openings 25. By way of these openings 25, a vacuum can be applied in the interior of the container 4.

The container 4 and the function module 5 are arranged on a common base plate 9. The base plate 9 essentially has the function of a base element for the container 4 and for the function module 5. The fluid line 7 and the hoses 29 and 32, respectively, extend partially through the base plate 9.

The container 4, the function module 5 and the base plate 9 constitute an integral unit in one piece. Particularly preferably, parts of this unit are produced by injection molding. These parts are in particular the side wall 38 and the rear wall 39, which are in one piece. The lid 37 can likewise be produced by injection molding, in which case the container 4 is completed by a welding and/or adhesive bonding method in which the lid 37 of the unit composed of side wall and rear wall 39 is welded on. In this context, reference is made to FIG. 4. At the front towards the function module 5, the receiving space 33 is closed by a lid 37. The lid 37 is connected to the container 4 by a welding and/or adhesive bonding method. An ultrasonic welding method is particularly preferably used.

It can also be seen from FIG. 3 that a handle 30 is integrally formed on the cassette module 1. With the handle 30, the operator can easily grasp the cassette module 1 and push it into, or remove it from, the container chamber 8 of the suction module 19.

The fluid line 7, which leads into the interior 33 of the container 4, comprises a hose section 10 which is guided over a concave rounding 11 on the function module, as is shown particularly clearly in FIGS. 4 and 5. The concave rounding 11 basically serves to receive a pump wheel (not shown here) of a peristaltic pump. The pump wheel protrudes into the concave rounding 11, in which case the pump wheel rotates with respect to the stationary hose section 10. The rotation movement generates a constant delivery of the medium located in the hose section 10.

Figure 7:
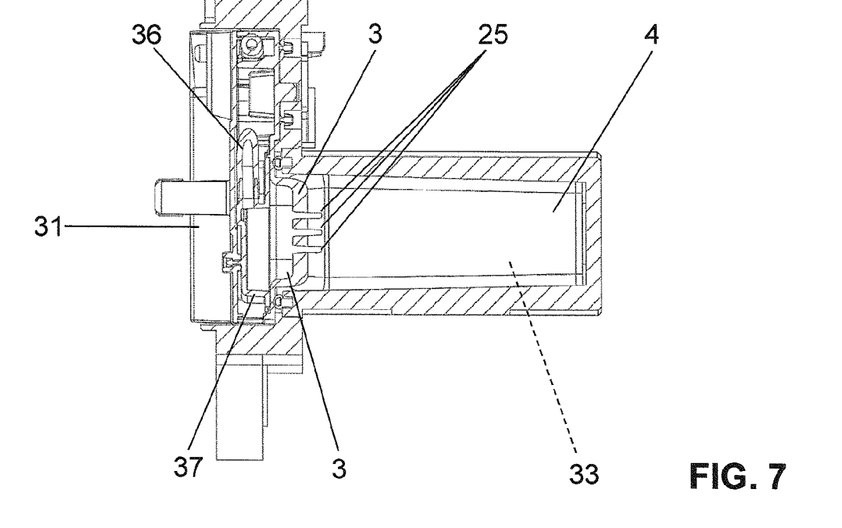
FIG. 7 shows a cross-sectional view along the section line A-A according to FIG. 1, together with the lid according to the variant of FIG. 4.
Figure 8:
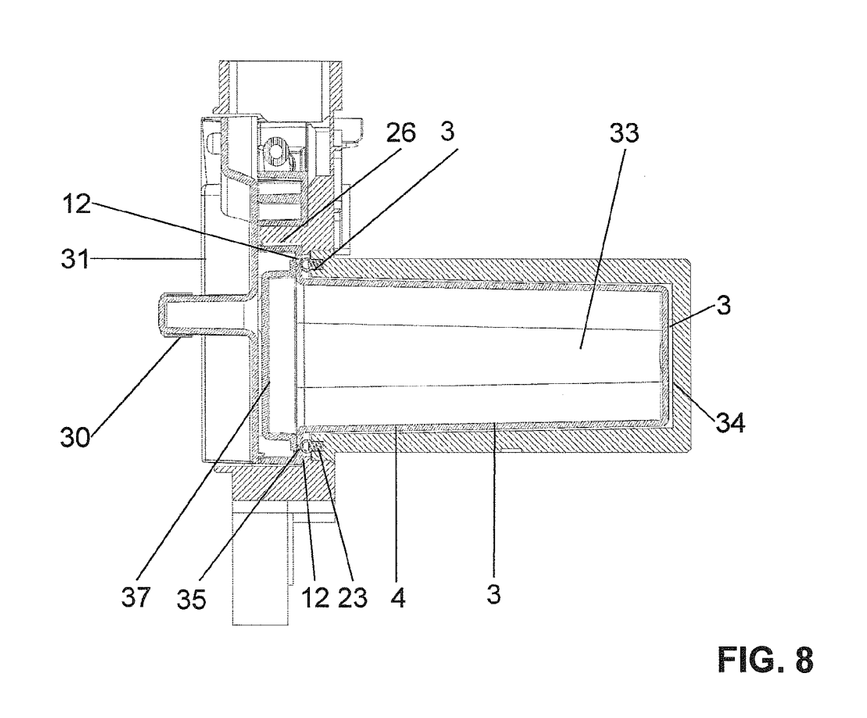
FIG. 8 shows a cross-sectional view along the section line B-B according to FIG. 1, together with the lid according to the variant of FIG. 4.

FIG. 7 shows a cross section along the section line A-A in FIG. 1, and FIG. 8 shows a cross section in the same plane, but at the height of the section line B-B.

It can be clearly seen in FIGS. 7 and 8 that the container walls 3 provide said container interior 33. It is also shown that towards the front the container interior 33 is closed by the lid 37. The lid 37 is connected to the container 4 by an ultrasonic welding 35, for example.

The container 4 moreover comprises a sealing surface 12, which is provided by a base plate 9 here. This sealing surface 12 is likewise shown clearly in FIG. 8. The sealing surface 12 cooperates with a sealing element 23, which is arranged on the suction module 19. A sealing action is thus provided between the sealing element 23 and the sealing surface 12. Alternatively, a seal can also be arranged on the sealing surface 12, which seal then cooperates with a corresponding sealing surface on the suction module 19. The seal can thus be arranged on the cassette module 1 and/or on the suction module 19.

As is shown in FIGS. 4 and 5, the fluid lines 7, 29 and 32 can be guided on the function module 5 by webs 14 protruding from a plate 9. The webs 14 can also be covered with a lid 31, for example.

Moreover, the cassette module 1 has an emergency drainage opening 16. The emergency drainage opening 16 is here provided as a break through the lid 37. The emergency drainage opening 16 provides a passage into the container interior 33 of the container 4. Should the container 4 be filled to a large degree during an operation, it is possible, during a pause in proceedings, for the operating personnel to remove the liquid from the interior 33 of the container 4 via a hose. The application of the vacuum to the container interior 33 is stopped for the duration of the emergency drainage.

FIGS. 7 and 8 show that the container chamber 8 has a shape identical to the outer shape of the container 4, or a complementary or matching shape. Thus, the container wall 3 of the container 4 bears on the chamber wall 17 of the container chamber 8. There is preferably a little play between the container wall 3 and the container chamber 8.

It can also be clearly seen from FIG. 2 that the suction module 19 here also comprises a plane wall 22 that extends around the container chamber 8. The seal 23 can be let into the plane wall 22 or can rest thereon. As is shown in FIG. 2, the seal 23 can be arranged on the suction module 19 or, alternatively, on the sealing surface 23 of the cassette module 1.

Moreover, the suction module 2 comprises an underpressure port 24 arranged in the chamber wall 17 of the container chamber 8, which underpressure port is connected to the pump. This underpressure port 24 is shown in FIG. 1. The underpressure port 24 is arranged such that it cooperates with the at least one vacuum opening 25 in the container wall 3 of the container 4. Preferably such that the at least one vacuum opening 25 in the container 4 comes to lie in the effective area of the underpressure port 24.

It can also be clearly seen from FIGS. 1 to 3 that the cassette module 1 can be pushed into the suction module 19 in a rectilinearly oriented insertion movement. When removing the cassette module 1 from the suction module 19 or from the container chamber 8 of the suction module 19, respectively, the cassette module 1 can be withdrawn again in the opposite direction.

In addition to the container chamber 8, the suction module 19 also comprises an additional chamber 26, into which the function module 5 can be pushed. This chamber 26 lies in front of the container chamber 8.

In conclusion, the cassette module 1 according to the invention has the advantage that it is of a very simple design and can be subjected to an underpressure in the container chamber by way of the vacuum opening.

The invention claimed is:

1. A suction system for receiving material and/or liquids aspirated during an operation, comprising a suction module, a cassette module, and a seal,
   wherein the suction module comprises a container chamber which is delimited by chamber walls and which is used for receiving parts of the cassette module, which container chamber is accessible via an insert opening, and a pump for generating an underpressure in the container chamber, and
   wherein said cassette module comprises:
      a container with a container wall that delimits a receiving space for receiving the material and/or the liquids, wherein the container can be inserted into the container chamber, and
      a sealing surface which extends around an outside of the container wall and by which a sealing action is provided between the container chamber and the container protruding into the container chamber,
   wherein the container has at least one inlet opening extending through the container wall, through which inlet opening the material and/or the liquid can be delivered to the receiving space of the container,
   wherein the container has at least one vacuum opening which extends through the container wall and by way of which the receiving space can be subjected to the underpressure built up in the container chamber, and
   wherein the suction module further comprises a plane wall extending around the insert opening, which provides a sealing surface extending around the container chamber for contact with the seal arranged in the area of the sealing surface of the cassette module.

2. The suction system according to claim 1, wherein the sealing surface runs in a plane which extends in an edge area through the container or which extends through a side wall of the container.

3. The suction system according to claim 1, wherein a seal extending around the container is arranged on the sealing surface, or wherein the sealing surface can be brought into contact with a seal arranged on the suction module.

4. The suction system according to claim 1, further comprising at least one port for connection to an operating system, which port opens into the inlet opening and connects a fluid line to the port.

5. The suction system according to claim 1, further comprising a function module, which is connected to the container, wherein, seen from the direction of the sealing surface, the container extends in a first direction and the function module extends in a second direction that is different from or counter to the first direction.

6. The suction system according to claim 1, wherein the container wall is provided with a comparatively thin wall thickness, wherein the wall thickness lies in the range of 0.5 to 1.5 mm.

7. The suction system according to claim 1, wherein, when the container is inserted in the container chamber of the suction module, the container wall lies at a distance from the walls of the container chamber, or wherein the container wall is supported by the container chamber.

8. The suction system according to claim 1, wherein the container is made of plastic and has an inherent stability, or wherein the container is made of plastic and has the form of a film.

9. The suction system according to claim 1, wherein a plurality of vacuum openings are arranged adjacent to one another, wherein the vacuum openings have the form of slits or circular openings.

10. The suction system according to claim 1, wherein the container delimiting the receiving space is provided by a circumferential side wall, a rear wall connected to the side wall, and a lid arranged opposite the rear wall, wherein the side wall and the rear wall are formed in one piece, and the lid is cohesively bonded to the side wall.

11. The suction system according to claim 1, wherein a fluid line comprises a hose section that is guided over a concave rounding on a function module, which rounding serves to receive a pump wheel of a peristaltic pump.

12. The suction system according to claim 4, wherein the fluid line is a hose section.

13. The suction system according to claim 6, wherein the wall thickness lies in the range of 0.7 to 1.2 mm.

14. The suction system according to claim 5, wherein a fluid line is guided on the function module partly by webs protruding from a plate, by a side wall lying on the webs and secured to the plate, or partly by webs protruding from a plate and by a side wall lying on the webs and secured to the plate.

15. The suction system according to claim 1, wherein the cassette module has an emergency drainage opening.

16. The suction system according to claim 5, wherein the function module is integrally formed on the container, wherein the function module is closed with a lid.

17. The suction system according to claim 1, wherein the insert opening of the container chamber is closed in an airtight manner by parts of the cassette module.

18. The suction system according to claim 1, wherein the container chamber has a shape identical to the outer shape of the container, such that the container wall of the container bears on the chamber wall, or wherein the container chamber has a shape similar to the outer shape of the container, in which case the container wall of the container lies at a distance from the chamber wall.

19. The suction system according to claim 1, wherein the suction module further comprises at least one underpressure port arranged in the chamber wall, wherein the underpressure port lies in the area of the at least one vacuum opening when the cassette module is inserted, and wherein the underpressure port is connected fluidically to the pump.

20. The suction system according to claim 1, wherein the cassette module can be pushed into the suction module in a rectilinearly oriented insertion movement.

21. The suction system according to claim 17, wherein the insert opening of the container chamber is closed in an airtight manner by a function module or a lid, or by a function module and a lid of the cassette module.

* * * * *